(12) United States Patent
Matsunaga et al.

(10) Patent No.: US 10,265,790 B2
(45) Date of Patent: Apr. 23, 2019

(54) WIRE ELECTRIC DISCHARGE MACHINE HAVING FUNCTION OF CLEANING INSIDE OF MACHINING TANK

(71) Applicant: FANUC Corporation, Yamanashi (JP)

(72) Inventors: Tomoaki Matsunaga, Yamanashi (JP); Akiyoshi Kawahara, Yamanashi (JP); Yasuo Nakashima, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 395 days.

(21) Appl. No.: 15/058,156

(22) Filed: Mar. 2, 2016

(65) Prior Publication Data

US 2016/0263687 A1 Sep. 15, 2016

(30) Foreign Application Priority Data

Mar. 13, 2015 (JP) .................................. 2015-50258

(51) Int. Cl.
*B23H 1/10* (2006.01)
*B23H 1/00* (2006.01)
(Continued)

(52) U.S. Cl.
CPC ............... *B23H 1/00* (2013.01); *B08B 3/024* (2013.01); *B08B 9/00* (2013.01); *B23H 1/10* (2013.01); *B23H 11/00* (2013.01); *B25J 9/1697* (2013.01); *B25J 11/0085* (2013.01); *G01N 21/94* (2013.01); *G06T 7/001* (2013.01); *B08B 9/093* (2013.01); *B23H 7/02* (2013.01);
(Continued)

(58) Field of Classification Search
CPC . B23H 1/10; B23H 1/00; B23H 11/00; B23H 7/02; B08B 9/00; B08B 3/024; B08B 9/093; B25J 9/1697; B25J 11/0085; B23Q 11/0042
USPC ......... 219/69.11, 69.12, 69.14, 76.14, 121.6, 219/121.61, 121.62, 121.67, 171.1
See application file for complete search history.

(56) References Cited

U.S. PATENT DOCUMENTS 5,140,124 A * 8/1992 Aso ..................... B23H 7/101
219/69.12
5,408,063 A 4/1995 Onishi
(Continued)

FOREIGN PATENT DOCUMENTS

DE 202007006113 U1 7/2007
JP 63-196326 A 8/1988
(Continued)

OTHER PUBLICATIONS

Extended European Search Report in EP Application No. 16159515. 2, dated Aug. 2, 2016.
(Continued)

*Primary Examiner* — Phuong T Nguyen
(74) *Attorney, Agent, or Firm* — Hauptman Ham, LLP (57) ABSTRACT

In order to prevent a reduction in the rate of operation and malfunction due to dirt in a machining tank, a wire electric discharge machine configured to perform electric discharge machining in the machining tank is provided with a camera for capturing an image of the inside of the machining tank and determining unit for detecting dirt in the machining tank based on the image captured by the camera. The dirt in the machining tank is detected by the determining unit.

5 Claims, 6 Drawing Sheets

(51) Int. Cl.
  *B23H 11/00* (2006.01)
  *B25J 9/16* (2006.01)
  *B25J 11/00* (2006.01)
  *G06T 7/00* (2017.01)
  *G01N 21/94* (2006.01)
  *B08B 3/02* (2006.01)
  *B08B 9/00* (2006.01)
  *B08B 9/093* (2006.01)
  *B23H 7/02* (2006.01)
  *G01N 21/90* (2006.01)

(52) U.S. Cl.
  CPC .... *G01N 21/90* (2013.01); *G05B 2219/40607* (2013.01); *G05B 2219/45221* (2013.01); *G06T 2207/30164* (2013.01); *Y02P 70/171* (2015.11)

(56) References Cited

U.S. PATENT DOCUMENTS

| | | | |
|---|---|---|---|
| 2001/0043735 A1* | 11/2001 | Smargiassi | G06T 7/0008 382/149 |
| 2008/0285840 A1 | 11/2008 | Kawai | |
| 2012/0103367 A1 | 5/2012 | Tang | |
| 2012/0152877 A1 | 6/2012 | Tadayon | |
| 2015/0241872 A1* | 8/2015 | Huang | G05B 19/4189 700/113 |

FOREIGN PATENT DOCUMENTS

| | | |
|---|---|---|
| JP | 7-256550 A | 10/1995 |
| JP | 8-197383 A | 8/1996 |
| JP | 11-104578 A | 4/1999 |
| JP | 2004-106142 A | 4/2004 |
| JP | 2004-268220 A | 9/2004 |
| JP | 2009-255223 A | 11/2009 |
| JP | 2015-24454 A | 2/2015 |

OTHER PUBLICATIONS

Office Action in JP Application No. 2015-050258, dated Mar. 28, 2017.

Office Action issued counterpart Chinese Application No. 201610144837.2, dated Jun. 6, 2018; 15 pages.

* cited by examiner

WIRE ELECTRIC DISCHARGE MACHINE HAVING FUNCTION OF CLEANING INSIDE OF MACHINING TANK

RELATED APPLICATIONS

The present application claims priority to Japanese Patent Application Number 2015-50258 filed Mar. 13, 2015, the disclosure of which is hereby incorporated by reference herein in its entirety.

BACKGROUND OF THE INVENTION

Field of the Invention

The present invention relates to a wire electric discharge machine having a function of cleaning a machining tank when the machining tank is contaminated with machining chips produced during electric discharge machining of a workpiece.

Description of the Related Art

A wire electric discharge machine applies voltage between a wire electrode and a workpiece disposed in a machining tank, thereby performing electric discharge machining of the workpiece. In this electric discharge machining, machining chips originating from the workpiece and the wire electrode are produced in each machining cycle. The machining chips are deposited on and contaminate a guide for applying the voltage to the wire electrode in the machining tank and a table on which the workpiece is set for the application of the voltage.

If the machining chips are left deposited on the guide and the table, they may cause improper voltage application between the wire electrode and the workpiece, so that it is important to clean the inside of the machining tank including the guide and the table.

Japanese Patent Application Laid-Open No. 2009-255223 discloses a technique in which abrasive particles and the like produced by water jet machining are removed from a machining tank by running water in a channel in the inner wall of the machining tank, in a multifunction machine for water jet machining and wire electric discharge machining.

In general, an operator cleans the inside of a machining tank after visually determining how machining chips are deposited in the machining tank, so that there may occur a reduction in the rate of operation of a machine and malfunction due to failure of cleaning. According to the technique disclosed in Japanese Patent Application Laid-Open No. 2009-255223 described above, it is impossible to automatically determine whether or not the inside of the machining tank is contaminated and clean the tank.

SUMMARY OF THE INVENTION

Accordingly, the object of the present invention is to provide a wire electric discharge machine having a function of cleaning the inside of a machining tank, capable of preventing a reduction in the rate of operation and malfunction due to dirt in the machining tank.

A wire electric discharge machine according to the present invention comprises a camera configured to capture an image of the inside of a machining tank and determining unit configured to detect dirt in the machining tank based on the image captured by the camera, the dirt in the machining tank being detected by the determining unit.

The wire electric discharge machine may further comprise a cleaning device configured to remove machining chips deposited in the machining tank and a robot comprising the camera and/or the cleaning device, and the machining chips in that position in the machining tank which corresponds to the image captured by the camera may be removed by the cleaning device when the dirt in the machining tank is detected by the determining unit.

The cleaning device may be configured to remove the machining chips by discharging a machining fluid as a cleaning solution by a machining fluid control pump as a drive source previously attached to the wire electric discharge machine.

In the wire electric discharge machine, a predetermined spot to be shot by the camera may be set in the machining tank or a mark may be provided on the predetermined spot, and the determining unit may be configured to determine whether or not the inside of the machining tank is contaminated, based on the image of the predetermined spot captured by the camera, an image of the predetermined spot on which the mark is provided, a reference image of the predetermined spot captured in advance, or a reference image of the mark.

The reference image may be updated, immediately after the machining chips are removed by the cleaning device, by the image of the predetermined spot captured by the camera or the image of the predetermined spot on which the mark is provided.

The determining unit may be configured to derive at least one of data related to a luminosity, color saturation, hue, and contrast from the image of the predetermined spot captured by the camera and determine whether or not the inside of the machining tank is contaminated, based on the derived data.

BRIEF DESCRIPTION OF THE DRAWINGS

The above and other objects and features of the present invention will be obvious from the ensuing description of embodiments with reference to the accompanying drawings, in which.

DETAILED DESCRIPTION OF THE PREFERRED EMBODIMENTS

Figure 1:
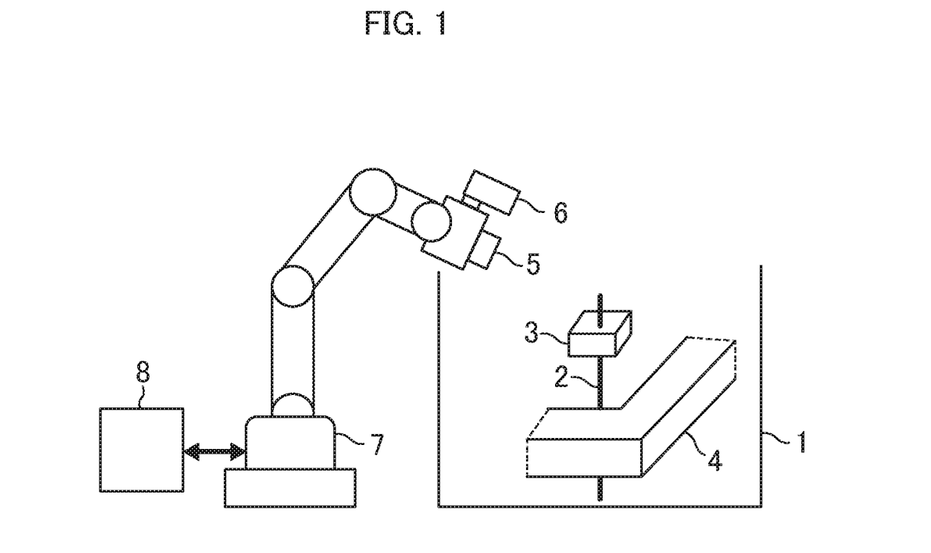
FIG. 1 is a view showing a part of the configuration of a wire electric discharge machine provided with a table on which a workpiece is set in a machining tank and a guide for applying voltage to a wire electrode.

Embodiments of the present invention will now be described with reference to the accompanying drawings. The present invention can be applied to an electric discharge apparatus provided with a machining tank and configured to perform electric discharge machining in the machining tank. In the following description, a wire electric discharge machine is given as an example. FIG. 1 is a view showing a part of the configuration of the wire electric discharge machine, comprising a table on which a workpiece is set in the machining tank and a guide for applying voltage to a wire electrode.

As shown in FIG. 1, the wire electric discharge machine comprises a table 4, on which a workpiece (not shown) is set in a machining tank 1, and a guide 3 for applying voltage to a wire electrode 2. The wire electric discharge machine is generally controlled by a controller 20 so that a machining fluid 16 is injected through the guide 3 as the electric discharge machining is performed. The electric discharge machining is performed in such a manner that the workpiece is disposed between the guide 3 and another guide (not shown) and voltage is applied to a machining gap defined by the wire electrode 2 and the workpiece. Machining chips 17 originating from the wire electrode 2 and the workpiece are produced during the electric discharge machining. The machining chips 17, which are collected together with the machining fluid in a sewage tank (not shown), adhere to the surfaces of the machining tank 1 and the guide 3 in the machining tank 1.

One embodiment of the wire electric discharge machine according to the present invention comprises a camera 5 for capturing an image of the inside of the machining tank 1 and a robot 7 mounted with a cleaning device 6 configured to inject a cleaning solution into the machining tank 1. A controller 8 controls the robot 7. Based on the image of the inside of the machining tank 1 captured by the camera 5, the controller 8 detects the deposition of machining chips on the guide 3 and the table 4. The controller 8 controls the cleaning device 6 to inject the cleaning solution and clean the guide 3, the table 4, and the inner wall of the machining tank 1. To clean the inside of the machining tank 1 means to clean the guide 3 and the table 4, as well as the inner wall of the machining tank 1.

In FIG. 1, the wire electrode 2 is stretched between the guide 3 and the other guide (not shown). Normally, however, the inside of the machining tank 1 is cleaned without the wire electrode 2 between the guides. Since the machining chips deposited in the machining tank 1 are automatically detected and cleaned by the robot 7, an operator's burden can be reduced, and a reduction in the rate of operation and malfunction due to failure of cleaning can be prevented. The controller 8 for the robot 7 and the controller 20 of the wire electric discharge machine exchange information with each other and are retracted to retracted positions so as not to hinder the electric discharge machining of the workpiece. In detecting or cleaning dirt in the machining tank 1, the controller 8 may be used to activate the robot 7 or control, in conjunction with the controller 20, the positions of the guide 3 and the like in the machining tank 1 so that the detecting or cleaning operation can be efficiently performed.

Figure 2:
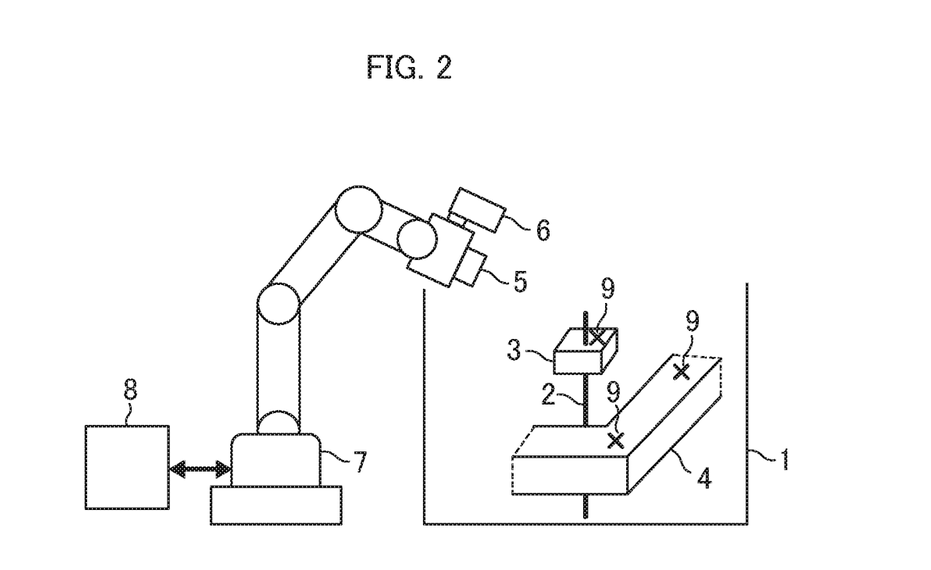
FIG. 2 is a view showing how marks for the detection of the deposition of machining chips by a camera are arranged on the surfaces of the guide and the table.

FIG. 2 is a view showing how marks for the detection of the deposition of machining chips by the camera are arranged on the surfaces of the guide and the table. As shown in FIG. 2, marks 9a for facilitating the detection of the deceleration of the machining chips 17 (see FIG. 5) are arranged on the surfaces of the guide 3 and the table 4. The camera 5 captures an image of an area in the machining tank 1 in which the marks 9a are arranged, and data on the captured image is delivered to the controller 8.

The controller 8 determines whether or not the marks 9a are hidden by dirt from the machining chips 17. If the marks 9a are hidden by the dirt, the inside of the machining tank 1 is cleaned by the cleaning device 6. The area in the machining tank 1 containing the marks is shot by the camera 5 after cleaning. If the marks 9a are still hidden, they are re-cleaned. If the marks 9a are recognized, the cleaning is completed. If the marks 9a are determined to be hidden without the installation of the cleaning device 6, an alarm signal may be given by the controller 8 to urge the operator to clean the inside of the machining tank 1.

Figure 3:
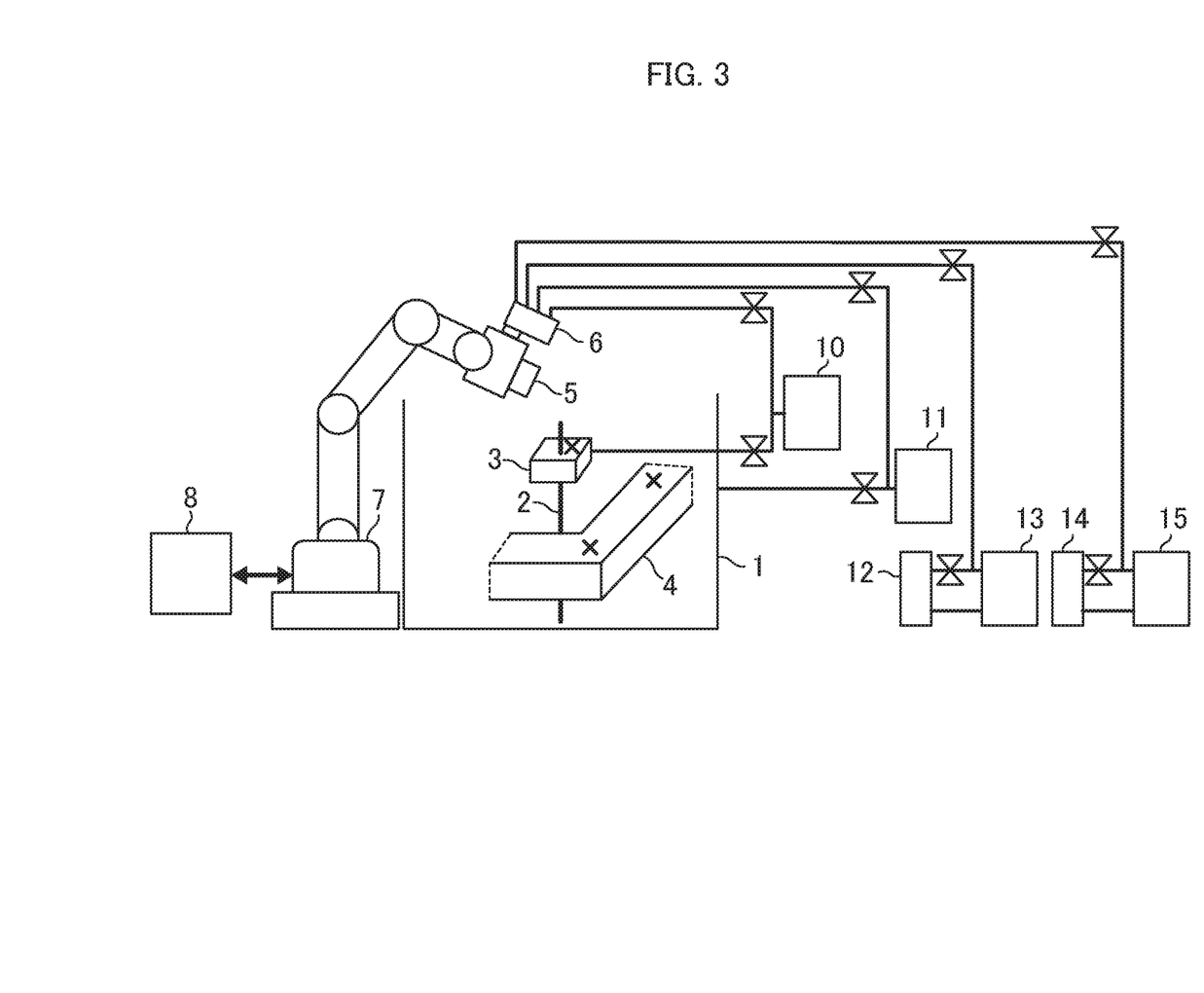
FIG. 3 is a diagram showing a drive source of a cleaning device.

FIG. 3 is a diagram showing a drive source of the cleaning device. The cleaning device 6 can clean the inside of the machining tank 1 with the machining fluid 16 used for the electric discharge machining. As shown in FIG. 3, any one of pumps 10, 11, 13 and 15, which are previously attached to the wire electric discharge machine, may be diverted to the drive source of the cleaning device 6. The pump 10 is used to discharge the machining fluid 16 into the machining gap (defined between the wire electrode 2 and the workpiece). The pump 11 is used to collect the machining fluid 16 in the machining tank 1. The pump 13 is used to circulate the machining fluid 16 in an ion-exchange resin 12 in order to adjust the specific resistance of the machining fluid. The pump 15 is used to circulate the machining fluid 16 through a filter 14 in order to remove impurities such as the machining chips 17 mixed in the machining fluid.

Figure 4A:
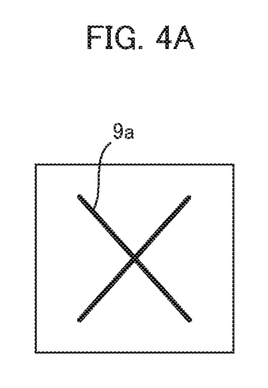
FIGS. 4A and 4B are diagrams showing an example of a mark for the detection of the deposition of machining chips.
Figure 4B:
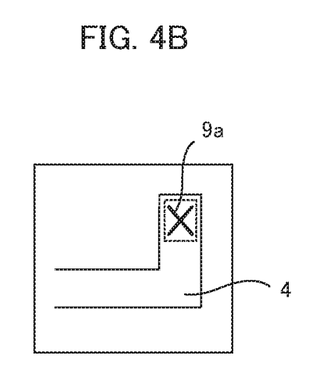

FIGS. 4A and 4B are diagrams showing an example of a mark for the detection of the deposition of machining chips. Whether or not the mark 9a is hidden is determined by storing an image of a previously prepared reference mark, such as that shown in FIG. 4A, in advance in a memory of the controller 8 and comparing the stored image of the reference mark with the actual captured image of the mark 9a (FIG. 4B). Based on this comparison, the deposition may be identified if the rate of concordance between the images is lower than a predetermined value. The mark may be formed of a groove or projection such that a decision can be made based on the extent to which it is filled.

Figure 5A:
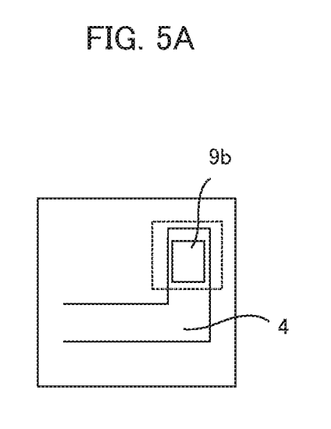
FIGS. 5A and 5B are diagrams showing an example in which a mark is formed by painting a predetermined area with a specified color.
Figure 5B:
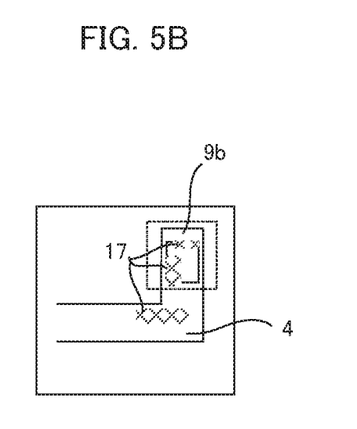

FIGS. 5A and 5B are diagrams showing an example in which the mark is formed by painting a predetermined area with a specified color. Further, a symbol such as the mark 9a may be replaced with a mark 9b with the specified color, as shown in FIG. 5A. If the color luminosity or pixel number is less than a reference value, it is determined that the colored area shown in FIG. 5B is narrower than a predetermined width, as shown in FIG. 5B, whereby the deposition of the machining chips 17 is identified. The reference mark is cleaned to overcome aging degradation of the guide 3 and the table 4. If this is done, an image of the reference mark captured on completion of the cleaning may be used for each cleaning cycle. The luminosity may be replaced with at least one of data related to the color saturation, hue, and contrast.

Figure 6A:
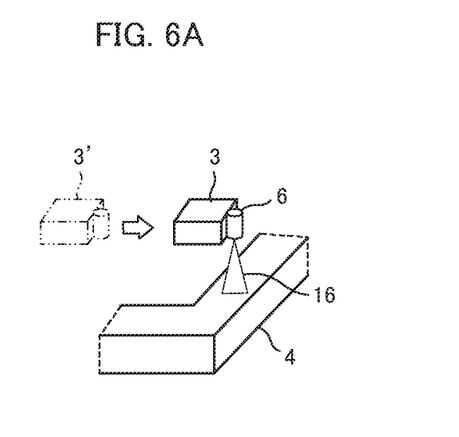
FIGS. 6A and 6B are diagrams showing an example in which the cleaning device is mounted on the guide.
Figure 6B:
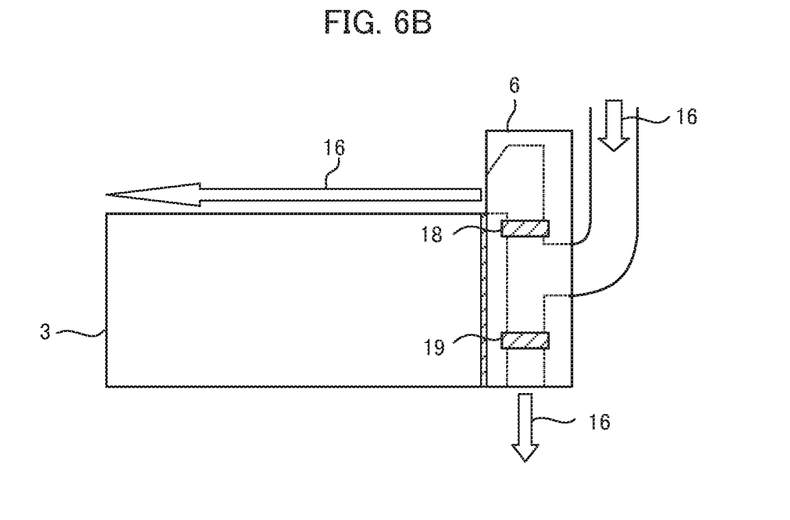

FIGS. 6A and 6B are diagrams showing an example in which the cleaning device is mounted on the guide. The cleaning device 6 and the camera 5 are not mounted on the robot 7, and the camera 5 is attached to the upper part of the machining tank 1 of the wire electric discharge machine and used to shoot the inside of the machining tank 1. As shown in FIG. 6A, the cleaning device 6 for injecting the machining fluid 16 is attached to the guide 3 so that the table 4 can be cleaned by moving the guide 3 to a position above the table 4. The guide 3 may be cleaned by pouring the cleaning solution (machining fluid 16) over its upper part, as shown in FIG. 6B. In cleaning only the guide 3 shown in FIG. 6B, the cleaning solution can be poured only over the guide 3 by closing a stopper 19. In cleaning only the table 4, in contrast, the cleaning solution can be poured only over the table 4 by closing a stopper 18. The machining fluid 16 for cleaning is supplied to the cleaning device 6 from the various pumps shown in FIG. 3.

Figure 7:
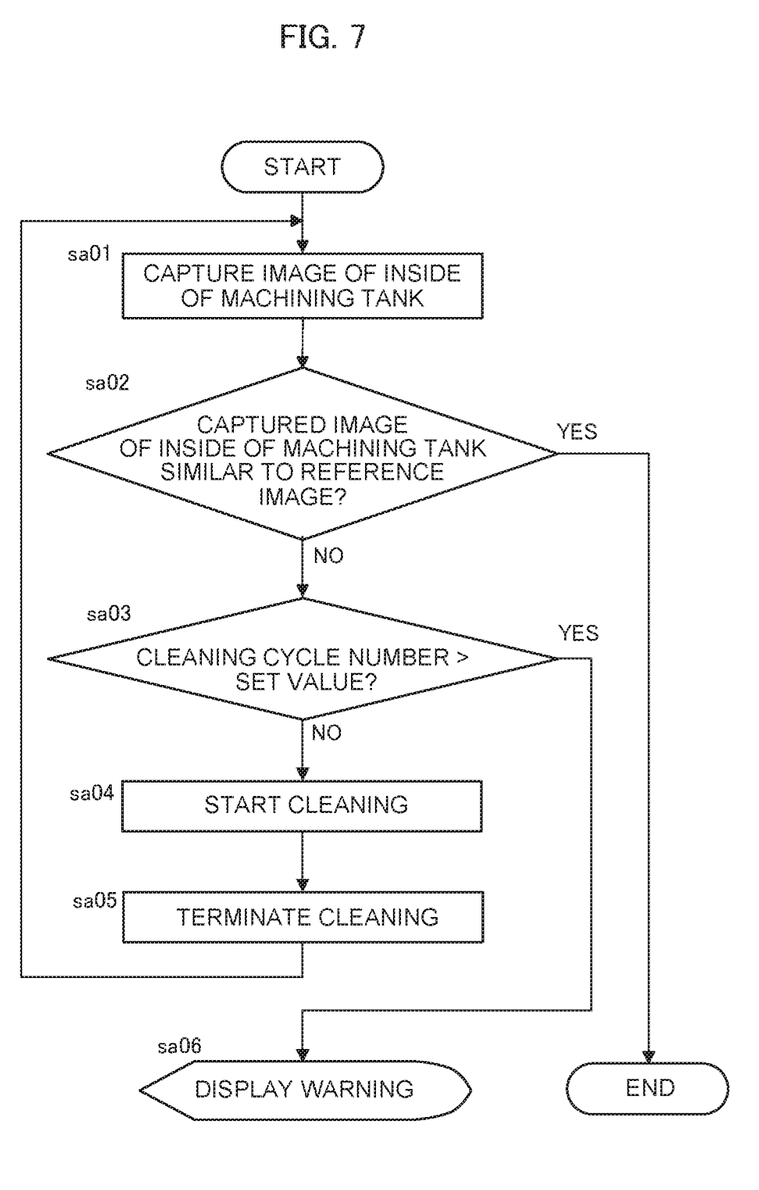
FIG. 7 is a flowchart illustrating a case in which a single inspection point is provided.

FIG. 7 shows a flowchart. The number of cleaning cycles is set in advance in preparation for any trouble such as the deposition of dirt that cannot be removed by the cleaning device 6. If the number of cleaning cycles exceeds a set value, the operation is terminated and a warning is issued. In this way, the cleaning can be prevented from being endlessly repeated. The following is a sequential description of various steps of processing.

[Step sa01] An image of the inside of the machining tank is captured.

[Step sa02] It is determined whether or not the captured image of the inside of the machining tank is similar to a reference image. If the images are similar (YES), it is determined that the inside of the machining tank is not contaminated, whereupon the processing ends. If not (NO), it is determined that the inside of the machining tank is contaminated with machining chips, and the processing proceeds to Step sa03.

[Step sa03] It is determined whether or not the set value is exceeded by the number of cleaning cycles. If the set value is exceeded (YES), the processing proceeds to Step sa06. If not (NO), the processing proceeds to Step sa04.

[Step sa04] Cleaning by the cleaning device is started.

[Step sa05] The cleaning by a predetermined cleaning operation is terminated, whereupon the processing returns to Step sa01.

[Step sa06] Since the dirt (machining chips) cannot be removed despite the cleaning by the cleaning device, a warning is displayed.

Step sa02 corresponds to "determining unit" described in Claims.

Figure 8:
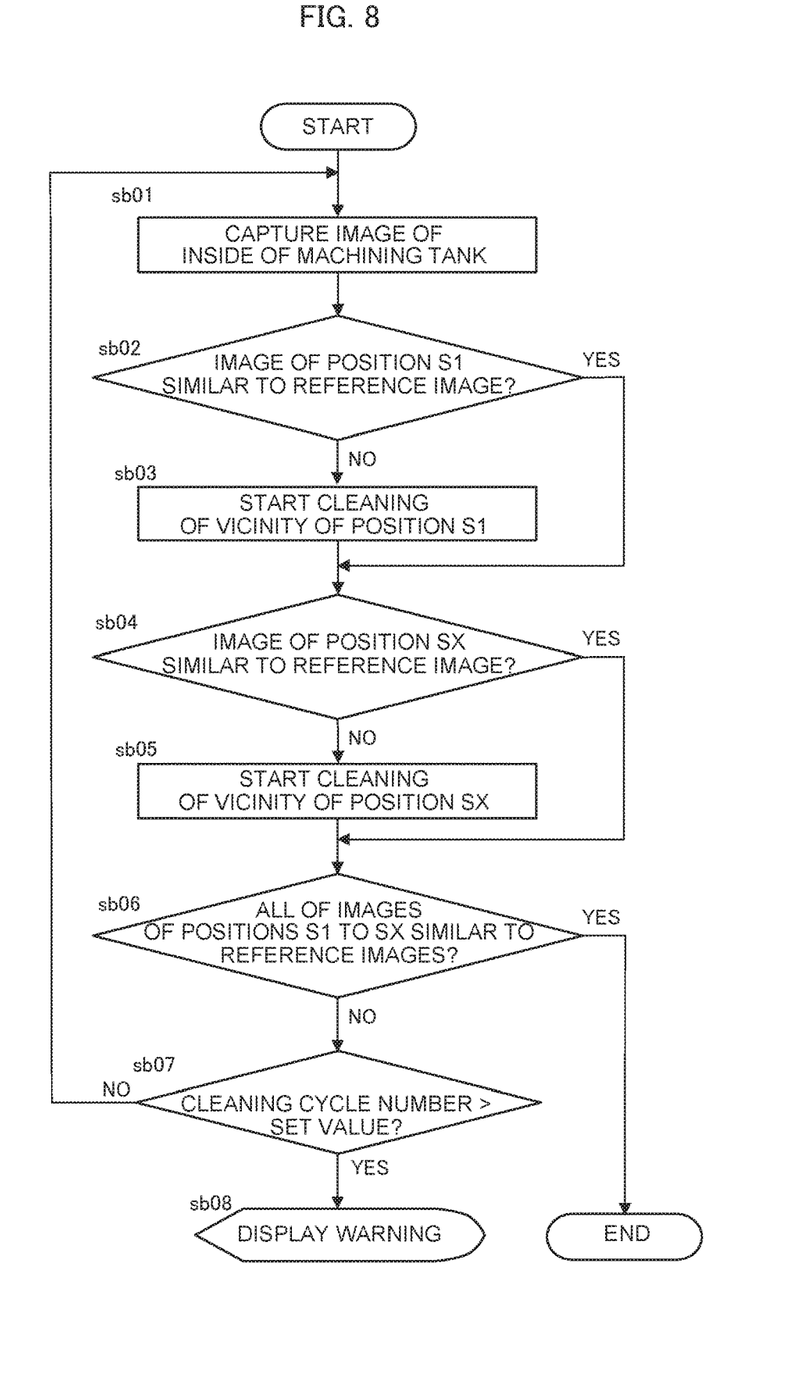
FIG. 8 is a flowchart illustrating a case in which a plurality of inspection points are provided.

FIG. 8 is flowchart illustrating a case in which a plurality of marks are arranged in various positions in the machining tank 1. Since the marks are located in the plurality of positions, each contaminated spot can be selectively cleaned. The following is a sequential description of various steps of processing.

[Step sb01] An image of the inside of the machining tank is captured.

[Step sb02] It is determined whether or not an image of a position S1 in the machining tank is similar to a reference image. If the images are similar (YES), the processing proceeds to Step sb04. If not (NO), the processing proceeds to Step sb03.

[Step sb03] Since it is determined in Step sb02 that the images are not similar, that is, the position S1 in the machining tank 1 is contaminated, cleaning of the vicinity of the position S1 is started.

[Step sb04] It is determined whether or not an image of a position SX in the machining tank is similar to a reference image. If the images are similar (YES), the processing proceeds to Step sb06. If not (NO), the processing proceeds to Step sb05. The determination on the similarity and the cleaning operation for other positions may be included in those for the positions S1 and SX.

[Step sb05] Since it is determined in Step sb04 that the images are not similar, that is, the position SX in the machining tank 1 is contaminated, cleaning of the vicinity of the position SX is started.

[Step sb06] It is determined whether or not all of images of the positions S1 to SX are similar to reference images. If all the images are similar (YES), then the positions S1 to SX in the machining tank are cleared of the dirt (machining chips 17), so that the processing ends. If all the images are not similar (NO), the processing proceeds to Step sa07.

[Step sb07] It is determined whether or not the set value is exceeded by the number of cleaning cycles. If the set value is not exceeded (NO), the processing returns to Step sb01. If the set value is exceeded (YES), the processing proceeds to Step sb08.

[Step sb08] Since the dirt (machining chips) cannot be removed despite the cleaning by the cleaning device, a warning is displayed.

Steps sb02, sb04 and sb06 correspond to "determining unit" described in Claims.

While an embodiment of the present invention has been described herein, the invention is not limited to the above-described embodiment and may be suitably modified and embodied in various forms.

The invention claimed is:

1. A wire electric discharge machine configured to perform electric discharge machining in a machining tank, the wire electric discharge machine comprising:
   a camera configured to capture an image of the inside of the machining tank;
   a controller configured to detect dirt in the machining tank based on the image captured by the camera; and
   a cleaning device configured to remove machining chips deposited in the machining tank;
   a robot comprising at least either the camera or the cleaning device,
   wherein
      the controller is further configured to operate the robot,
      a mark is provided on a predetermined spot captured by the camera, and the controller determines whether or not the inside of the machining tank is contaminated, based on the image of the predetermined spot captured by the camera and a reference image of the mark, and
   the controller is further configured to operate the robot in such a manner that the machining chips in the location in the machining tank which corresponds to the image captured by the camera are removed by the cleaning device when the machining tank is determined to be contaminated by the controller.

2. The wire electric discharge machine according to claim 1, wherein detection of dirt in the machining tank by the controller and removal of machining chips by the cleaning device are repeated.

3. The wire electric discharge machine according to claim 1, wherein the cleaning device is configured to remove the machining chips by discharging a machining fluid as a cleaning solution by a machining fluid control pump as a drive source previously attached to the wire electric discharge machine.

4. The wire electric discharge machine according to claim 1, wherein the reference image is updated, immediately after the machining chips are removed by the cleaning device, by the image of the predetermined spot captured by the camera or the image of the predetermined spot on which the mark is provided.

5. The wire electric discharge machine according to claim 1, wherein the controller is configured to derive at least one of data related to a luminosity, color saturation, hue, and contrast from the image of the predetermined spot captured by the camera and determine whether or not the inside of the machining tank is contaminated, based on the derived data.

* * * * *